United States Patent
Siebels

[11] Patent Number: 5,306,310
[45] Date of Patent: Apr. 26, 1994

[54] VERTEBRAL PROSTHESIS

[75] Inventor: Wolfgang Siebels, Deggendorf, Fed. Rep. of Germany

[73] Assignee: MAN Ceramics GmbH, Deggendorf, Fed. Rep. of Germany

[21] Appl. No.: 937,345

[22] Filed: Aug. 27, 1992

[30] Foreign Application Priority Data

Aug. 27, 1991 [DE] Fed. Rep. of Germany ....... 4128332

[51] Int. Cl.$^5$ .............................................. A61F 2/28
[52] U.S. Cl. .................................................... 623/17
[58] Field of Search ...................... 606/60, 61; 623/17, 623/18

[56] References Cited

U.S. PATENT DOCUMENTS

| 4,309,777 | 1/1982 | Patil ....................................... 606/61 |
| 4,553,273 | 11/1985 | Wu ......................................... 606/61 |
| 4,554,914 | 11/1985 | Kapp et al. . | |
| 4,932,975 | 6/1990 | Main et al. . | |
| 4,938,768 | 7/1990 | Wu ......................................... 606/60 |
| 4,961,740 | 10/1990 | Ray et al. ............................... 606/61 |
| 5,055,104 | 10/1991 | Ray ........................................ 606/61 |

FOREIGN PATENT DOCUMENTS

| 3023942 | 6/1980 | Fed. Rep. of Germany . | |
| 4012622 | 4/1990 | Fed. Rep. of Germany . | |
| 1222260 | 4/1986 | U.S.S.R. ................................ 606/60 |

Primary Examiner—David Isabella
Attorney, Agent, or Firm—Robert W. Becker & Associates

[57] ABSTRACT

A prosthesis as a vertebral replacement element consists of two helical strands, which may are screwed together to form a tubular structure. The implant is inserted between vertebrae and then slightly unscrewed until the desired height is reached. The helical strands consist of carbon fiber reinforced composite material.

8 Claims, 1 Drawing Sheet

VERTEBRAL PROSTHESIS

BACKGROUND OF THE INVENTION

The present invention relates to a vertebral prosthesis comprised of essentially two generally cylindrical members, which are connected by means of a screw mechanism in such a manner that the overall axial length of the connected members can be varied.

U.S Pat. No. 4,554,914 describes a vertebral prosthesis of this type which consists of a first male screw-like element and a second female tubular element with an internal screw thread. After screwing one element into the other, the assembly constitutes a pin-like support, whose free ends taper to points for penetrating the adjacent vertebrae. As a vertebral prosthesis two such pins are arranged adjacent to each other to function as distance pieces between two healthy vertebrae. In order to prevent shearing forces in the known design the adjacent vertebrae are additionally anchored with plates.

One object of the present invention is to provide a vertebral prosthesis of the aforementioned type the implantation of which does not require additional anchoring means and is easily performed.

SUMMARY OF THE INVENTION

In order to achieve these and/or other goals apparent from the specification, claims and drawings, the two members are inventively constituted by helically formed springs, the two helical springs having approximately the same diameter, and can be screwed into each other to form a tubular structure.

The helical members are designed to have a diameter which is similar to the diameter of the vertebrae so that skewed positioning or shearing movements are prevented.

The design in accordance with the invention offers the further advantage that the vertebral prosthesis may be manufactured by a simple production technology from metal or synthetic resin with or without fiber reinforcement.

In accordance with a further possible advantageous development of the invention the helical members are produced by impregnating a fiber strand with a matrix material resulting in a fiber reinforced composite material. It is preferred to use carbon fibers for reinforcement.

In order to ensure axial engagement of the assembled helical springs it is advantageous that the cross section of the strand, which may contain fibers, be rectangular. In this embodiment, with a respective shaping of the cross section and a suitable selection of the helix angle, it is possible by assembling of the two members to produce a tubular structure or hollow cylinder, which has a continuous wall with cylindrical inner and outer mantle surfaces. The two ends may respectively be so designed that they form an elastic zone in order to emulate the elasticity of the bone.

For the axial anchoring of the screwed together helical springs it is possible to provide a support sleeve, which after the assembly of the helical strands of the prosthesis or vertebral replacement element is inserted into the resulting tubular structure. This anchoring function may also be performed by a curable bone cement, with which the cavity of the tubular structure of the prosthesis is filled.

In accordance with a further possible advantageous embodiment of the invention at least one of the two members has support elements, with which the two members are radially anchored when they have been screwed into each other. Such joint may for instance be in the form of a tongue and groove joint, an annular shoulder or the like. Such support elements may be simply provided along the entire helical spring or only at sections thereof.

The prosthesis in accordance with the invention offers the further advantage that only an assortment of helical strands with different diameters has to be stocked. The height or axial length of the prosthesis of two assembled helical springs is produced by cutting to the required length. The ends are then covered with end plates, which are clamped or glued in place and which on their outer surface have anchoring means for cooperation with an adjacent vertebral bone.

BRIEF DESCRIPTION OF THE DRAWINGS

The invention will now be described in more detail with reference to the working embodiments illustrated in diagrammatic drawings, in which.

DESCRIPTION OF PREFERRED EMBODIMENTS

Figure 1:
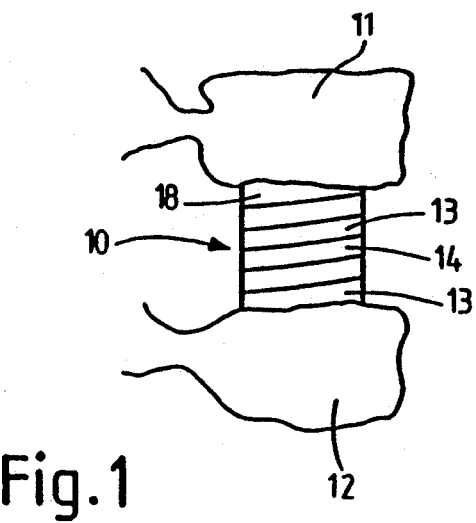
FIG. 1 shows a first working embodiment of the invention.
Figure 3:
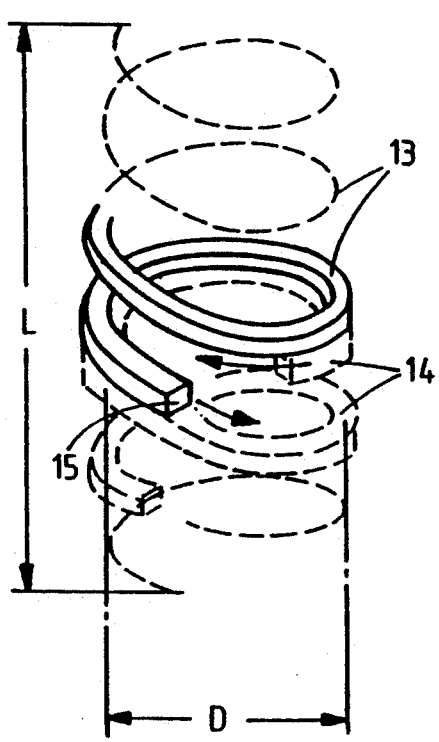
FIG. 3 illustrates the screwing together of the helical springs.

FIG. 1 shows a vertebral prosthesis or implant 10, which is arranged between two vertebrae 11 and 12. The implant 10, as shown in FIG. 3 in more detail, is comprised of two members, each member being in the form of a helical strand 13 and 14 resembling helical springs. The helical springs 13 and 14 have the same mean diameter D. The selection of the diameter of the helical springs depends on the dimensions of the adjacent vertebrae 11 and 12. For the different dimensions of the vertebrae of one patient or of different patients an assortment of helical strands with suitable different diameters must be stocked.

Figure 2:
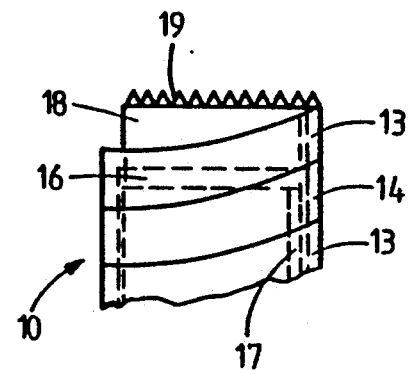
FIG. 2 shows anchoring means in the form of spikes.

In order to produce a vertebral prosthesis or implant 10 two helical springs 13 and 14 with the same diameter are screwed into each other as indicated by the arrows in FIG. 3. By suitably designing the cross section 15 and the helix angle of a strand it is possible to ensure that the helical springs 13 and 14 make more or less gapfree contact with each other so that the prosthesis or implant 10 resembles a compressed compression spring. The two helical springs 13 and 14 are screwed into each other until the necessary length L is reached and subsequently the strands may be cut to the desired length. In a vertebra prosthesis produced in this manner the helical springs 13 and 14 are connected as illustrated in FIGS. 1 and 2. For a radial anchoring of the helical springs a sleeve 17 is inserted into the interior 16 of the implant 10. The two ends are provided with an end plate 18, which after cutting the tubular structure to the desired length may be clamped, inserted or glued in place. In the case of the afore-described working embodiment with the inserted sleeve 17, the support sleeve 17 may function as an abutment for the end plates 18 so that neither a clamping nor a bonding step is necessary. The outer end face of the end plates 18 is provided with anchoring means such as projections 19, roughed areas, spikes or the like, which fix the prosthesis 10 between the adjacent vertebrae 11 and 12.

Figure 4A:
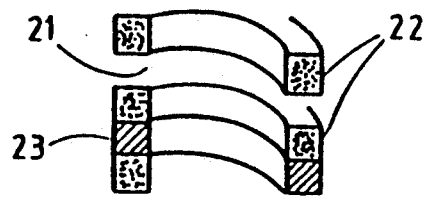
FIG. 4a shows two helical springs with planar, radially extending surfaces.

For implantation the two helical springs 13 and 14, suitably cut to length, are completely screwed into each other, the end plates 18 are inserted and the prosthesis or vertebral implant 10 is placed between the vertebrae 11 and 12. Then the two helical members 13 and 14 are unscrewed to such an extent that the vertebral prosthesis 10 is adapted to the final intermediate distance between the vertebrae. When this is done a gap 21 is produced between adjacent turns of the spring at the end as shown in FIG. 4a. Such gaps may be employed for the insertion of bone cement into the cavity 16 of the prosthesis 10. When using bone cement or bone material it is furthermore possible to omit the end plates 18. In cooperation with the bone cement the gap 21 of the vertebral prosthesis may provide for elasticity therein that corresponds to the elasticity of the bone. Axial elasticity may furthermore be ensured by making the cross section of at least one of the helical strands smaller at the ends so that between adjacent helices gaps are left at end zones of the implant. These end zones then function as helical springs.

The cross section 15 of the helical strands or springs 13 and 14 is preferably rectangular. However, its configuration may be freely selected as desired, and for instance more particularly shapes or projections may be selected which function as a radial anchoring of the two helical strands 13 and 14.

Figure 4B:
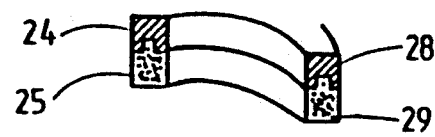
FIG. 4b shows a design with tongue and groove joints between the helical springs.
Figure 4C:
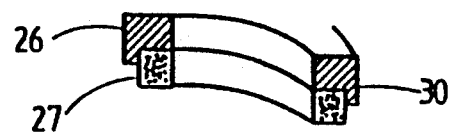
FIG. 4c shows a working embodiment with interlocked helical springs.

FIGS. 4b and 4c show two such working embodiments. In accordance with FIG. 4b the radial anchoring means consists of a tongue 29 on the helical strand 25 and of a groove 28 in the helical strand 24. On screwing the two strands 24 and 25 together the tongue 29 will extend into the groove 28 so that the two helical members 24 and 25 are radially locked in relation to each other.

The anchoring means may be provided on only one of the strands 26 as illustrated in FIG. 4c. Such means may for instance be a shoulder 30 which is in engagement with the outer periphery of the second strand 27.

The helical strands 13, 14 and, respectively, 22, 23, 25, 26 and 27 may be produced from materials conventional for endoprostheses. They preferably consist of fiber reinforced composite materials, wherein both the fibers and the matrix are biocompatible. Especially suitable are carbon fibers which are impregnated and drawn through a die as a bundle. In the partly cured condition the impregnated bundle is shaped into the helical form and then fully cured. The form or mold corresponds to the cross section of the fiber strand, and the radial support elements 28 through 30 are directly shaped in this step. It is furthermore possible to form endless long helical strands of different cross sections to be stocked from which the implants are cut to length as necessary.

The present invention is, of course, in no way restricted to the specific disclosure of the specification and drawings, but also encompasses any modifications within the scope of the appended claims.

What I claim is:

1. An implantable vertebral prosthesis configured to be inserted between adjacent vertebrae comprising:
   a biocompatible tubular structure with a hollow interior space having a variable length, said tubular structure being formed from two helical springs having substantially equal diameters, said helical springs being connected to each other by screwing one of said helical springs into the other of said helical springs, whereby said length of said tubular structure may be adjusted to a final intermediate distance between the vertebrae by screwing or unscrewing said two helical springs.

2. A vertebral prosthesis according to claim 1, wherein said helical springs are comprised of fiber reinforced composite material.

3. A vertebral prosthesis according to claim 1, wherein said helical springs have a rectangular cross-section.

4. A vertebral prosthesis according to claim 1, wherein said tubular structure has a tubular wall that is gapfree after said helical springs are screwed into one another.

5. A vertebral prosthesis according to claim 1, wherein at least one of said helical springs comprises a support element for radially anchoring said helical springs relative to one another.

6. A vertebral prosthesis according to claim 1, further comprising a support sleeve disposed within said hollow interior space for radially supporting said helical springs relative to one another.

7. A vertebral prosthesis according to claim 1, further comprising end plates, attached to each free end of said tubular structure, for cooperating with adjacent vertebrae.

8. A vertebral prosthesis according to claim 1, further comprising means for the introduction of bone cement and bone substance into said hollow interior space of said tubular structure.

* * * * *